(12) United States Patent
Koduri

(10) Patent No.: US 9,664,574 B2
(45) Date of Patent: May 30, 2017

(54) THERMOMETER DEVICE AND METHOD OF MAKING

(71) Applicant: Sreenivasan K Koduri, Allen, TX (US)

(72) Inventor: Sreenivasan K Koduri, Allen, TX (US)

(73) Assignee: TEXAS INSTRUMENTS INCORPORATED, Dallas, TX (US)

(\*) Notice: Subject to any disclaimer, the term of this patent is extended or adjusted under 35 U.S.C. 154(b) by 451 days.

(21) Appl. No.: 14/272,450

(22) Filed: May 7, 2014

(65) Prior Publication Data

US 2015/0036719 A1  Feb. 5, 2015

Related U.S. Application Data

(60) Provisional application No. 61/860,106, filed on Jul. 30, 2013.

(51) Int. Cl.
| G01K 13/00 | (2006.01) |
| G01K 1/14 | (2006.01) |
| G01K 1/18 | (2006.01) |

(52) U.S. Cl.
CPC ............ *G01K 13/002* (2013.01); *G01K 1/14* (2013.01); *G01K 1/18* (2013.01); *G01K 13/004* (2013.01); *Y10T 29/49002* (2015.01)

(58) Field of Classification Search
CPC .................................................. G01K 13/004
See application file for complete search history.

(56) References Cited

U.S. PATENT DOCUMENTS

| 5,792,070 A * | 8/1998 | Kauphusman ........... A61B 5/01 600/549 |
| 6,676,290 B1 * | 1/2004 | Lu ............................ G01K 1/18 374/163 |
| 6,694,172 B1 * | 2/2004 | Gagnon ................ G01T 1/2928 250/363.02 |
| 7,316,507 B2 * | 1/2008 | Sisk ......................... G01K 1/14 374/100 |
| 2011/0245713 A1 * | 10/2011 | Rensen .................... A61B 5/01 600/549 |
| 2011/0249699 A1 * | 10/2011 | Bieberich .............. G01K 1/165 374/1 |

FOREIGN PATENT DOCUMENTS

DE  EP 1039281 A1 *  9/2000  ............... G01K 1/16

\* cited by examiner

*Primary Examiner* — Clayton E Laballe
*Assistant Examiner* — Leon W Rhodes, Jr.
(74) *Attorney, Agent, or Firm* — Tuenlap D. Chan; Charles A. Brill; Frank D. Cimino

(57) ABSTRACT

A method of manufacturing a thermometer probe includes: obtaining a hollow housing having an open end and a curved inner surface; obtaining a flexible detecting component having an adhesive layer; obtaining an insertion component; detachably attaching the flexible detecting component to the insertion component; inserting the insertion component, having the flexible detecting component attached thereto, through the open end of the hollow housing and into the hollow housing such that the adhesive layer is disposed between the insertion component and the inner surface; and adhering, via the adhesive layer, the flexible detecting component to the curved inner surface.

3 Claims, 10 Drawing Sheets

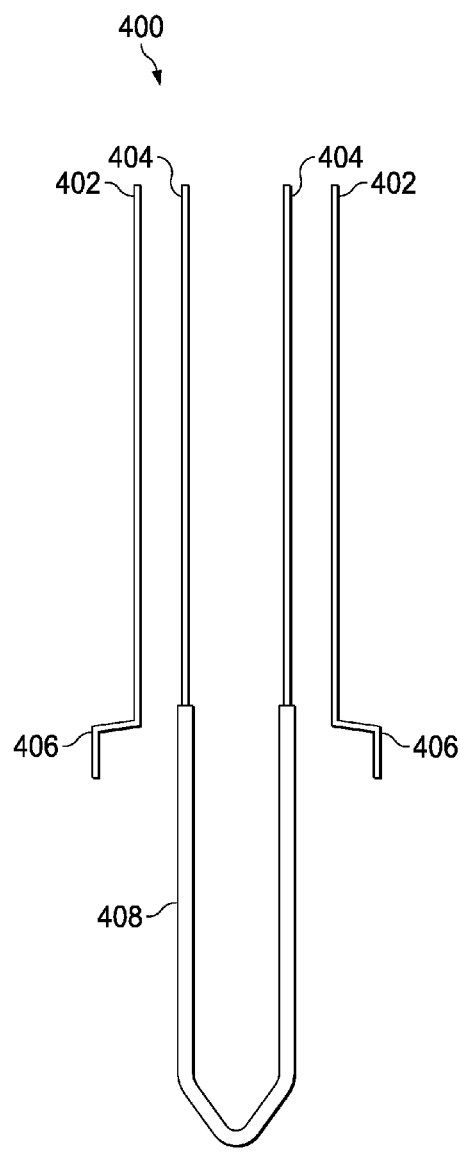
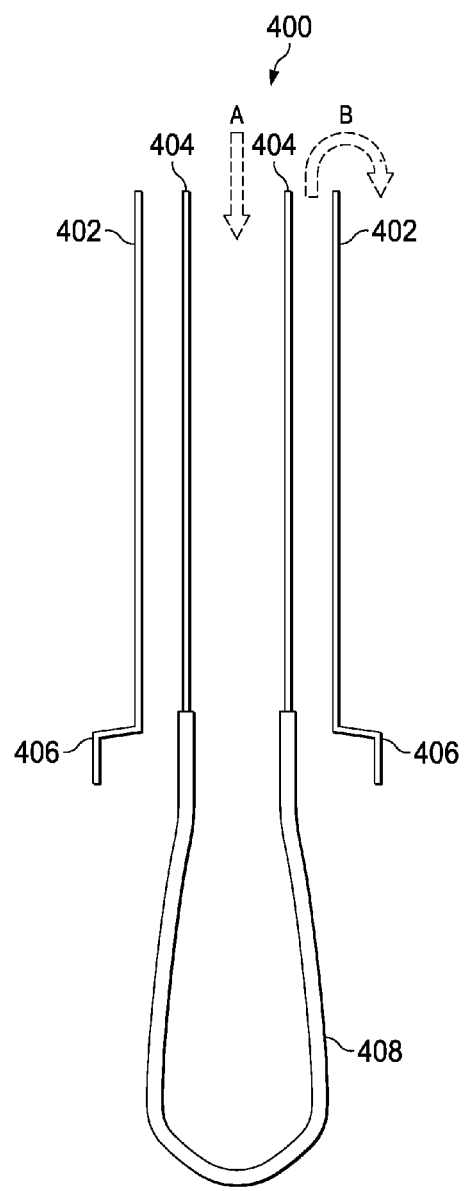
FIG. 4A
FIG. 4B

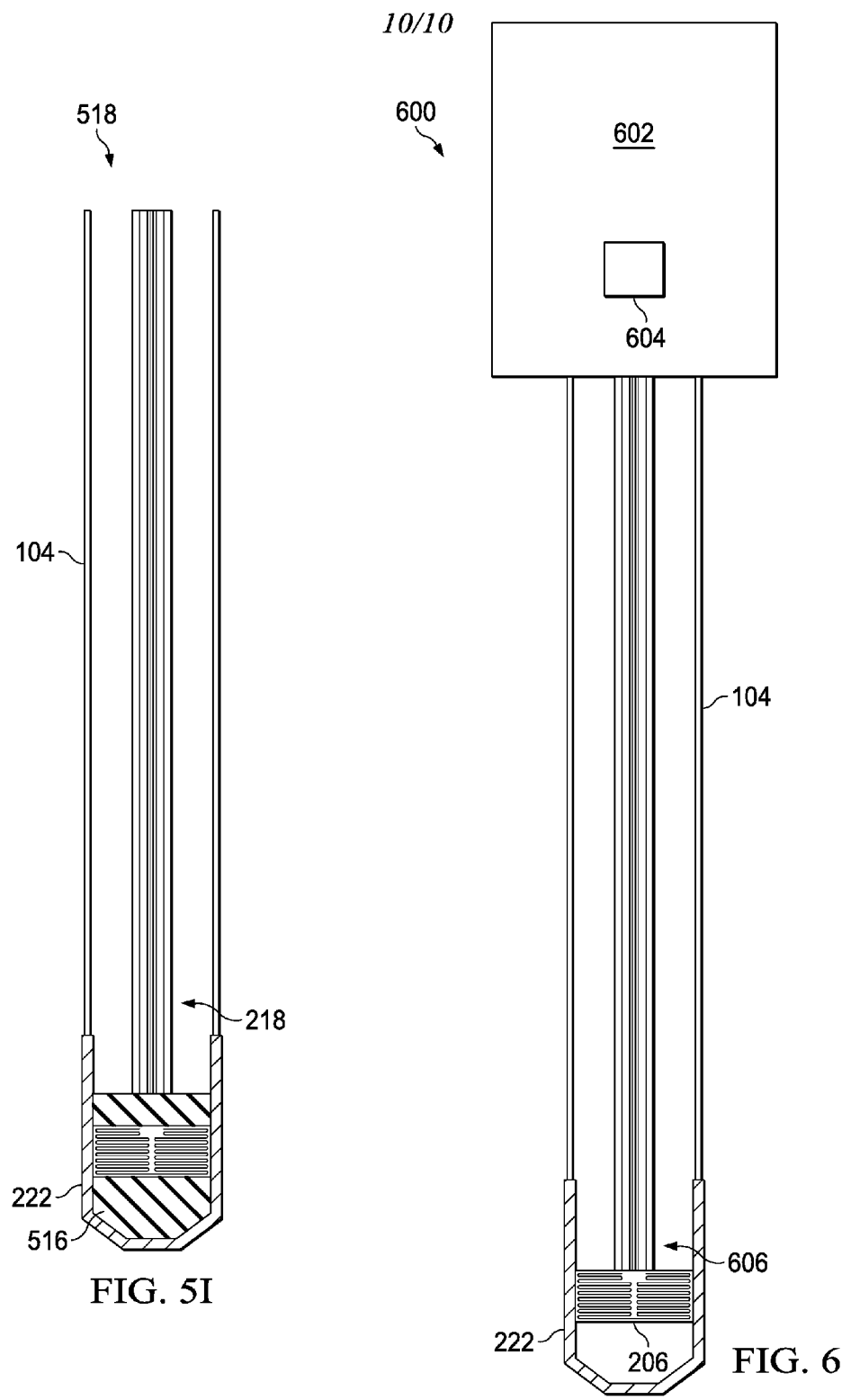

THERMOMETER DEVICE AND METHOD OF MAKING

The present application claims priority from: U.S. Provisional Application No. 61/860,106 filed Jul. 30, 2013, the entire disclosure of which is incorporated herein by reference.

BACKGROUND

The present invention relates to a thermometer device and a method of manufacturing a thermometer device.

Conventional thermometer devices are designed to sense the temperature of the desired object and display the temperature to the user. In some cases, the thermometer is preheated close to a target temperature (for example, the temperature of the human body) such that the time required to obtain the final temperature is minimized.

Such thermometers, while being fast and convenient to use, are generally difficult to manufacture, requiring intricate assembly steps that are time consuming and costly.

FIG. 1A illustrates a conventional thermometer device 100.

As shown in the figure, device 100 includes probe housing 102, probe 104, probe tip 110, flexible cable 106 and connector 108.

Probe tip 110 serves to sense the surrounding temperature. Probe tip 110 will be described in greater detail with reference to FIG. 1B. Probe 104 connects to probe tip 110 and probe housing 102. Probe 104 is typically manufactured from metal or any other material that is a good heat conductor. Probe housing 102 connects to flexible cable 106, and flexible cable 106 connects to connector 108.

In operation, when a practitioner desires to take the temperature of a patient, connector 108 is plugged into a display module (not shown) that is capable of reading and displaying the temperature at probe tip 110. When the display module is activated, probe tip 110 is preheated to a temperature close to the target temperature of the patient. For example, the target temperature may be 96.5° Fahrenheit. Once preheated, probe tip 110 is placed at the location from which the temperature reading is desired. The temperature at the desired location is transmitted from probe tip 110, to probe 104, to probe housing 102, to flexible cable 106, to connector 108 and finally to the display module, where the temperature is displayed to the practitioner.

FIG. 1B illustrates probe tip 110 of device 100.

Probe tip 110 includes a temperature sensor 112, sensor wires 114, a heating element 116 and heating element wires 118.

Temperature sensor 112 may be a thermistor, thermocouple or any other device that can accurately sense temperature in an area. Temperature sensor 112 is attached to the inside surface of probe tip 110, which is typically a labor-intensive process that requires very skilled workers and is not totally repeatable from one device to the next. The process is manual and requires an operator to use very small tools, so placing temperature sensor 112 in the same location, with the same surface area contact to probe tip 110 every time is very difficult and time consuming. Sensor wires 114 connect temperature sensor 112 to a control module (not shown) in probe housing 102.

Heating element 116 may be a resistor, etched foil, nichrome, or any other element that can rapidly heat a surface. Like temperature sensor 112, heating element 116 is also attached to the inside surface of probe tip 110, which again is typically a labor-intensive process that requires very skilled workers and is not totally repeatable from one device to the next. Heating element wires 118 connect heating element 116 to the control module (not shown) in probe housing 102.

In operation, when the connector 108 is plugged into the display module and the display module is powered on the control module in probe housing 102 provides power to heating element 116. As probe tip 110 begins to heat up, temperature sensor 112 relays temperature signals via sensor wires 114 to the control module. A feedback loop is thus created between the control module, heating element 116 and temperature sensor 112 such that probe tip 110 can be preheated to within a few degrees of an expected (normal) temperature and maintain that temperature until it is ready to use on a patient.

When it is ready for patient use, the practitioner will place probe tip 110 in the target area, and temperature sensor 112 will sense the surrounding temperature, which will typically be higher than the preheated temperature. The display module will continue to read data regarding the temperature of the target area until the temperature reading reaches a steady state, at which point probe tip 110 has reached the temperature of the target area. The display module will then display the temperature of the target area for the practitioner to read.

What is needed is a temperature sensing device that is simple to manufacture, has a manufacturing process that may be automated and that evenly and quickly preheats.

BRIEF SUMMARY

The present invention provides temperature sensing device that is simple to manufacture, has a manufacturing process that may be automated and that evenly and quickly preheats.

In accordance with aspects of the present invention, method of manufacturing a thermometer probe includes: obtaining a hollow housing having an open end and a curved inner surface; obtaining a flexible detecting component having an adhesive layer; obtaining an insertion component; detachably attaching the flexible detecting component to the insertion component; inserting the insertion component, having the flexible detecting component attached thereto, through the open end of the hollow housing and into the hollow housing such that the adhesive layer is disposed between the insertion component and the inner surface; and adhering, via the adhesive layer, the flexible detecting component to the curved inner surface.

Additional advantages and novel features of the invention are set forth in part in the description which follows, and in part will become apparent to those skilled in the art upon examination of the following or may be learned by practice of the invention. The advantages of the invention may be realized and attained by means of the instrumentalities and combinations particularly pointed out in the appended claims.

BRIEF SUMMARY OF THE DRAWINGS

The accompanying drawings, which are incorporated in and form a part of the specification, illustrate example embodiments and, together with the description, serve to explain the principles of the invention. In the drawings:

FIGS. 4A-B illustrate an insertion component used in manufacturing a temperature sensing device in accordance with aspects of the present invention;

FIG. 5I illustrates a final assembly configuration of a temperature sensing device in accordance with aspects of the present invention; and FIG. 6 illustrates an alternate assembly configuration for a temperature sensing device in accordance with aspects of the present invention.

DETAILED DESCRIPTION

The present invention is drawn to a flexible heating element for use in a temperature sensing device and a method of assembling the temperature sensing device having the flexible heating element. A flexible circuit includes both the beating element and the temperature sensing element for use within the hollow probe tip the temperature sensing device. The flexible circuit can be bent without any effects detrimental to the function of either the heating element or the temperature sensing element. Further, because it is flexible, the heating element may conformingly affix to the curved inner surface of the probe tip.

During assembly, the flexible circuit can be bent for easy insertion into the probe tip. In some embodiments an assembly tool, which includes an expandable section, may be used. In a specific embodiment, the expandable section may be an inflatable balloon. The flexible circuit and inflatable balloon are then inserted into a temperature probe for deployment of the flexible circuit. The inflatable balloon is inflated until the flexible circuit contacts the inner surface of the probe. An adhesive on the flexible circuit serves to adhere the flexible circuit to the inner surface of the probe. The balloon is then deflated and removed.

The assembly method described above provides for much easier manufacturing than conventional methods. Using a flexible circuit allows for much more consistency in the preheating and temperature sensing elements, since they can be assembled without restrictions from the temperature probe. In addition, utilizing the inflatable balloon allows for consistent attachment of the flexible circuit to the probe, such that a more reliable temperature sensing device can be manufactured.

Example aspects of the present invention will now be further described with reference to FIGS. 2A-6.

FIGS. 2A-F illustrate planar views of an example manufacturing process of a flexible circuit in accordance with aspects of the present invention.

Figure 1A:
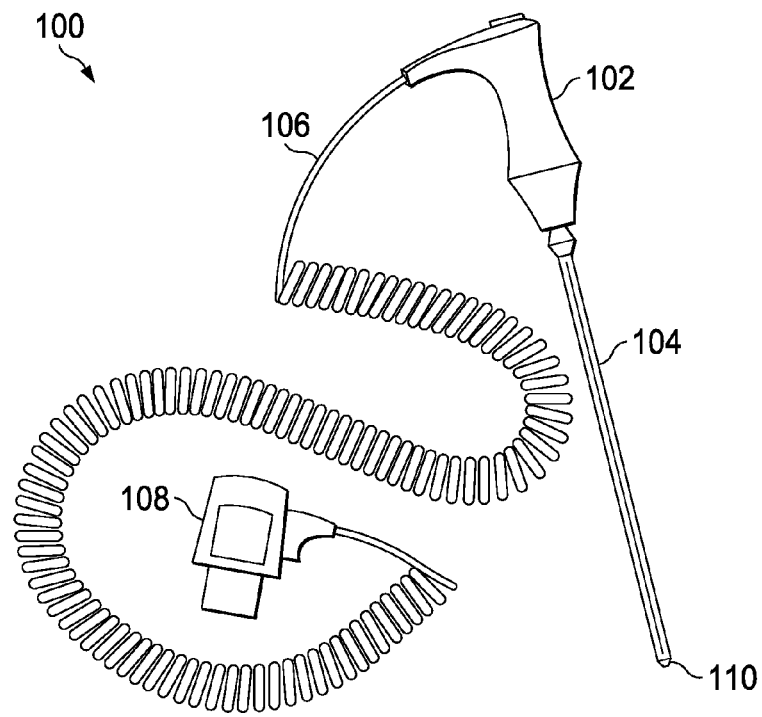
FIGS. 1A-B illustrate a conventional thermometer device.
Figure 1B:
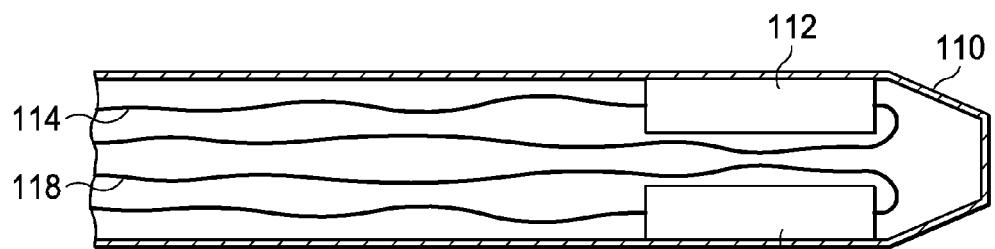
Figure 2A:
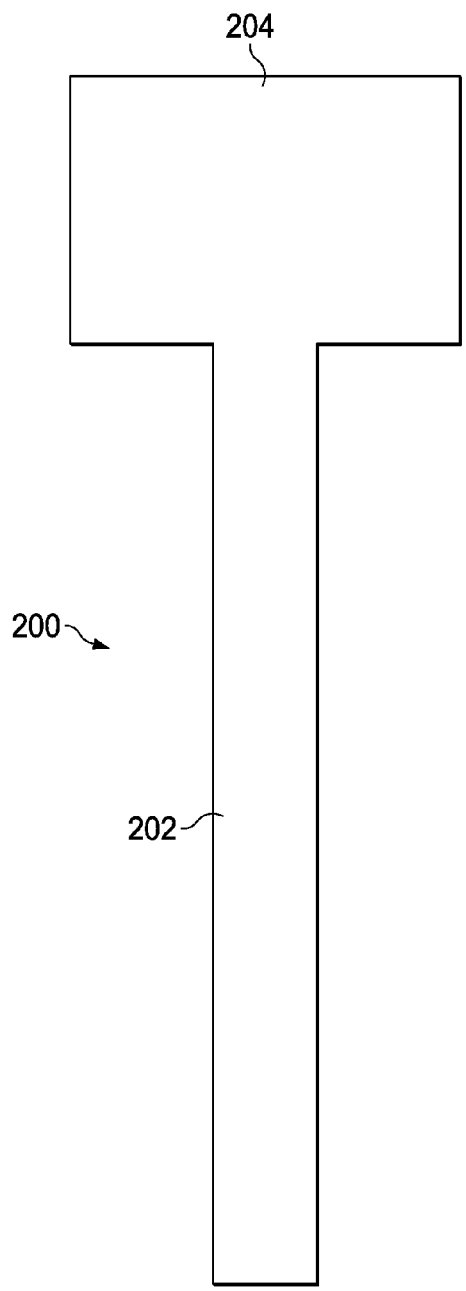
FIGS. 2A-F illustrate planar views of an example manufacturing process of a flexible circuit in accordance with aspects of the present invention.

FIG. 2A illustrates a first step in an example manufacturing process of a flexible circuit in accordance with aspects of the present invention.

As shown in the figure, a flexible circuit base 200 is provided. Flexible circuit base 200 includes supply portion 202 and head portion 204. Flexible circuit base 200 may be constructed from polyimide, PEEK, polyester, polyethylene napthalate, polyetherimide, FEP or any other material that is able to provide a flexible substrate. Flexible circuit base 200 may include a removable film that when removed, exposes an adhesive layer.

Figure 2B:
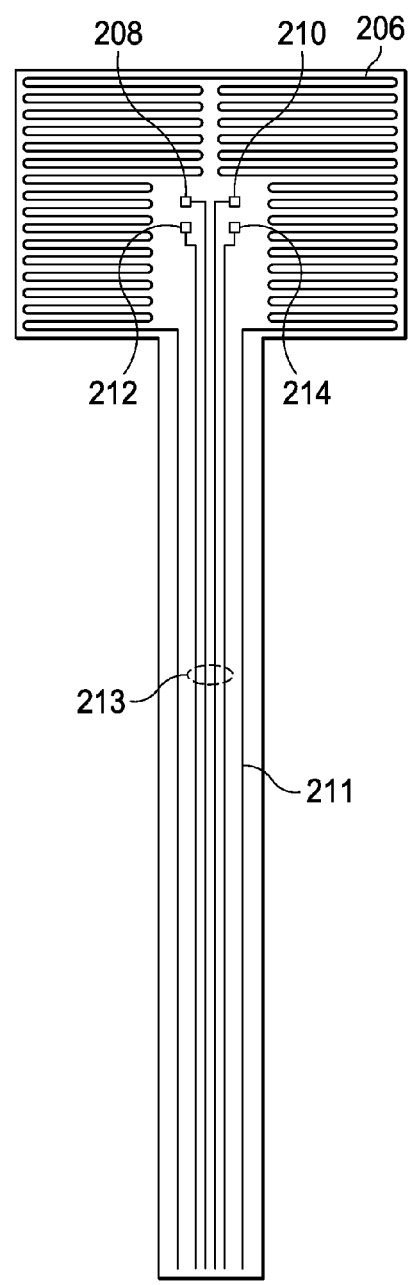

FIG. 2B illustrates a second step in an example manufacturing process of a flexible circuit in accordance with aspects of the present invention.

As shown in the figure, the second step includes adding heating element 206 and sensor attachments 208-214 to flexible circuit base 200. Probe housing 102 provides power to heating element 206 by way of power line 211, which extends from supply portion 202. Probe housing 102 additionally communicates with sensor attachments 208-214 via wires 213 that extend from head portion 204.

Heating element 206 may be a conductive material that is able to conduct current in order to generate resistive heat. In some embodiments, heating element 206 may be constructed from resistance wire that is disposed on flexible circuit base 200. In some embodiments, heating element 206 may be deposited by any known deposition method, a non-limiting example of which includes chemical vapor deposition. In this example embodiment, heating element 206 is a serpentine winding of a portion of power line 211. In other non-limiting examples, heating element may be any arrangement, coiling or winding of power line 211. Heating element 206 is located on head portion 204 and is operable to preheat a temperature sensing device when the device is fully assembled. The distribution of power line 211 enables a relatively quick and distributed heating of the area of head portion 204.

Sensor attachments 208-214 may be conductive pads that are disposed to provide a base to which a sensor will be subsequently attached. In some embodiments, sensor attachments 208-214 may be constructed from a conductive material that is disposed on flexible circuit base 200. In some embodiments, sensor attachments 208-214 may be deposited by any known deposition method, a non-limiting example of which includes chemical vapor deposition. In some embodiments, sensor attachments 208-214 may be located on head portion 204, while in other embodiments, sensor attachments 208-214 may be located on supply portion 202.

The heating element 206 is shown in one configuration in FIG. 2B, however it can be appreciated that heating element 206 may be disposed on flexible circuit base 200 in any other pattern that would provide heat in accordance with aspects of the present invention. In addition, sensor attachments 208-214 are also disposed on flexible circuit base 200. In this example, sensor attachments 208-214 are arranged in a particular configuration. However, sensor attachments 208-214 may be arranged in any other configuration that would enable connection of a temperature detecting device in accordance with aspects of the present invention.

Figure 2C:
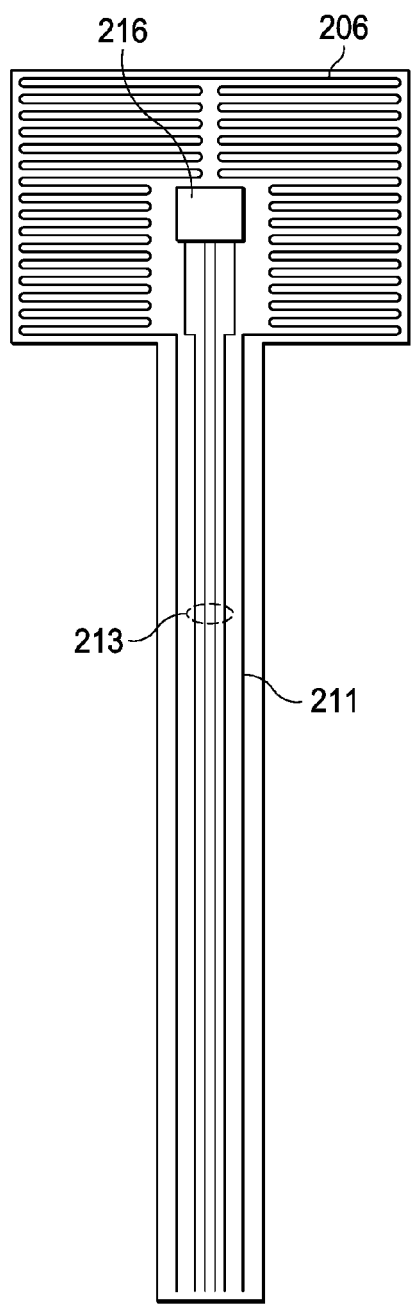

FIG. 2C illustrates a third step in an example manufacturing process of a flexible circuit in accordance with aspects of the present invention.

As shown in the figure, the third step includes adding a temperature sensor 216. Temperature sensor 216 is attached to sensor attachments 208-214 (not shown) by any known method or system, a non-limiting example of which includes an adhesive.

Figure 2D:
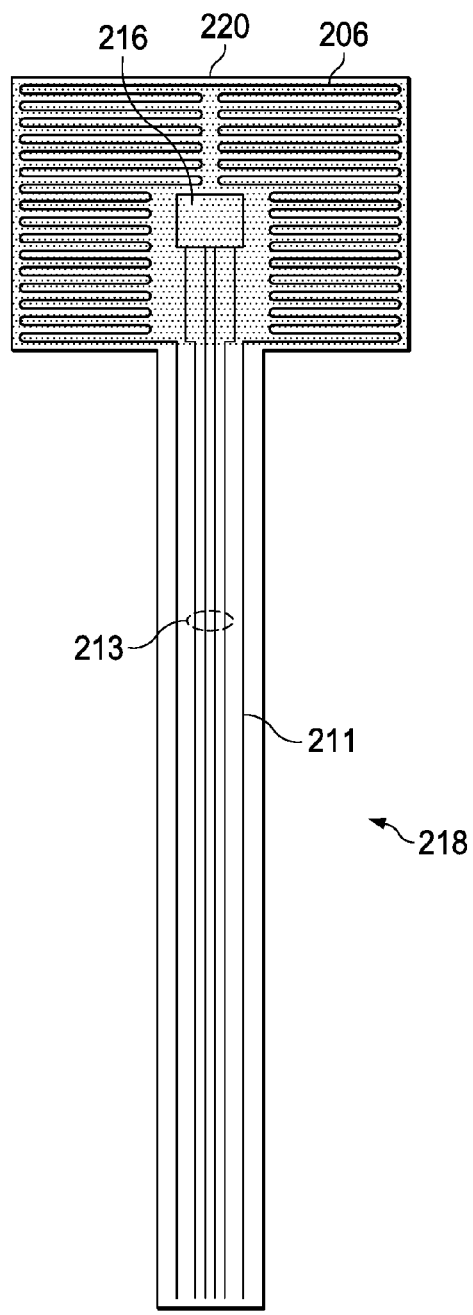

FIG. 2D illustrates a fourth step in the example manufacturing process of a flexible circuit in accordance with aspects of the present invention.

As shown in the figure, the fourth step includes adding adhesive layer 220 on top of heating element 206 and temperature sensor 216 to create an attachable flexible circuit 218. Adhesive layer 220 provides adhesion while still allowing the assembly to remain flexible.

Figure 2E:
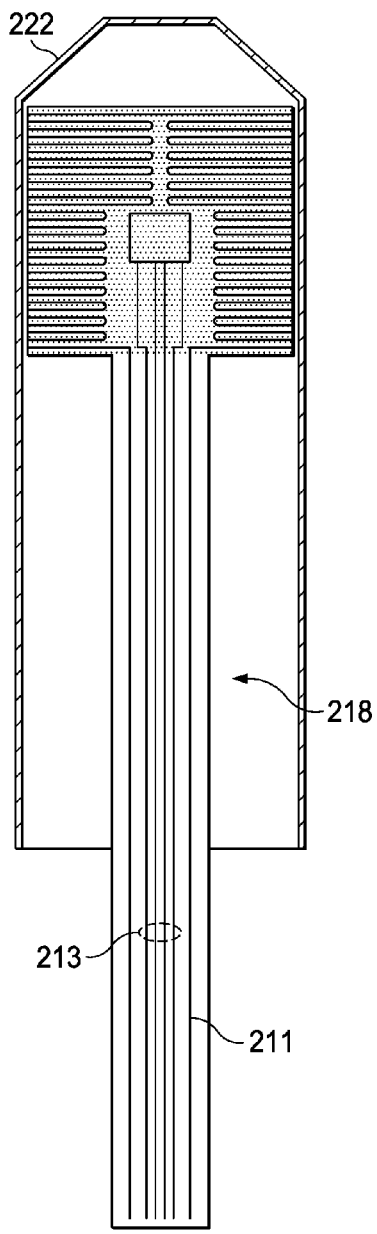

FIG. 2E illustrates attachable flexible circuit 218 being attached to the inside surface of a probe tip 222.

As shown in the figure, flexible circuit 218 is conformingly adhered to the curved inner surface of probe tip 222 using a method that will be described in more detail with reference to FIGS. 5A-F. In general, adhesive layer 220 is conformingly adhered to the inner surface of probe tip 222 such that flexible circuit 218 is in conforming contact with the curved inner surface of probe tip 222.

Figure 2F:
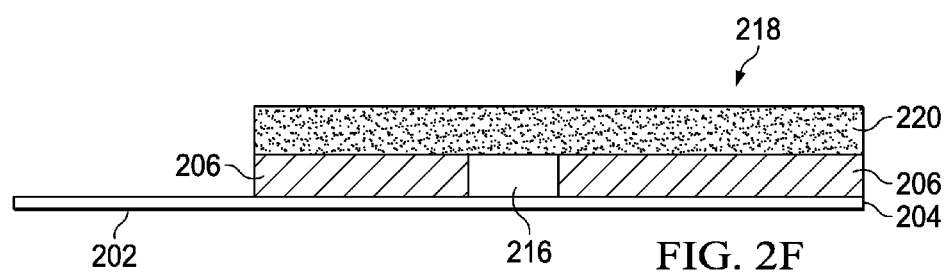

FIG. 2F illustrates a cross sectional view of flexible circuit 218.

As shown in the figure, heating element 206 and temperature sensor 216 are disposed on head portion 204 of flexible circuit 218. Adhesive layer 220 is disposed on heating element 206 and temperature sensor 216. Adhesive layer 220 is a relatively weak adhesive that enables flexible circuit 218 to be detachably fixed to an insertion component to aid in assembly such that neither heating element 206 nor temperature sensor 216 are damaged during the insertion or detachment process. The insertion component and its interaction with flexible circuit 218 will be further described with reference to FIGS. 4A-B and 5A-E.

Additional example embodiments of a flexible circuit in accordance with aspects of the present invention will now be described with reference to FIGS. 3A-C.

Figure 3A:
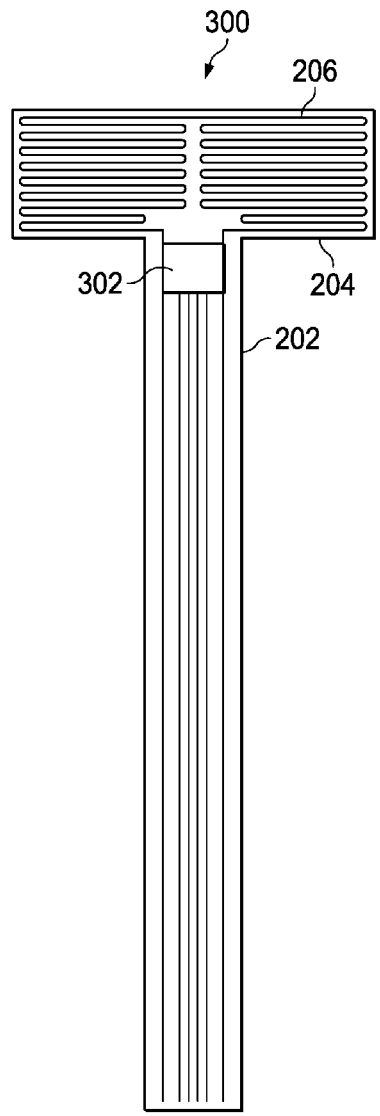
FIGS. 3A-C illustrate alternative embodiments of the manufacturing process described with reference to FIGS. 2A-E.

FIG. 3A illustrates another example embodiment of a flexible circuit 300 in accordance with aspects of the present invention.

As shown in the figure, flexible circuit 300 is similar to flexible circuit 218. However, flexible circuit 300 includes a temperature sensor 302 that is located in a different position than temperature sensor 212 of flexible circuit 218. Providing temperature sensor 302 on supply portion 202 instead of head portion 204 may allow heating element 206 to reach the desired temperature earlier since more surface area of head portion 204 would be covered by heating element 206.

Figure 3B:
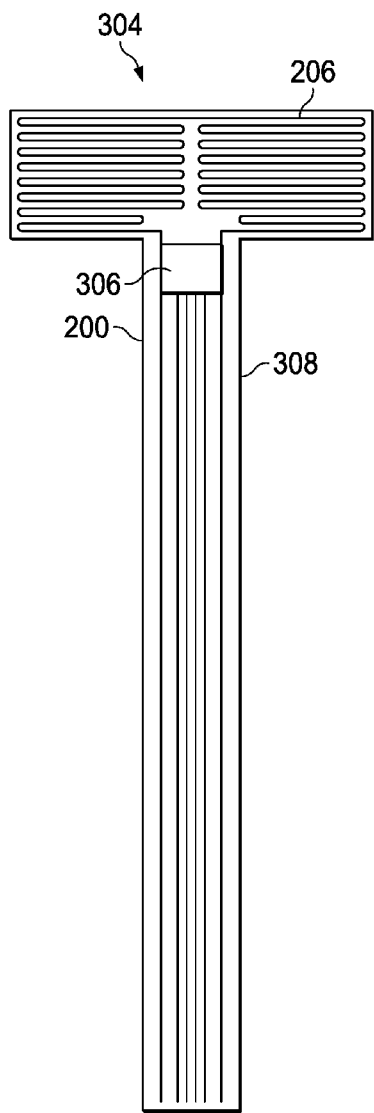

FIG. 3B illustrates another example embodiment of a flexible circuit 304 in accordance with aspects of the present invention.

As shown in the figure, temperature sensor 306 is located in a different position than shown in FIG. 2C, as described with reference to FIG. 3A. It is also located on a separate flexible circuit base 308 that is disposed on top of heating element 206, and heating element 206 is disposed on flexible circuit base 200. Thus, the circuit can be manufactured by disposing temperature sensor 306 on flexible circuit base 308, and separately disposing heating element 206 on flexible circuit base 200. Then, flexible circuit base 308 may be disposed on top of flexible circuit base 200, or vice versa, to create flexible circuit 304. Manufacturing the circuit in this manner may simplify the assembly by only requiring one component to be adhered to each of flexible circuit bases 200 and 308.

Figure 3C:
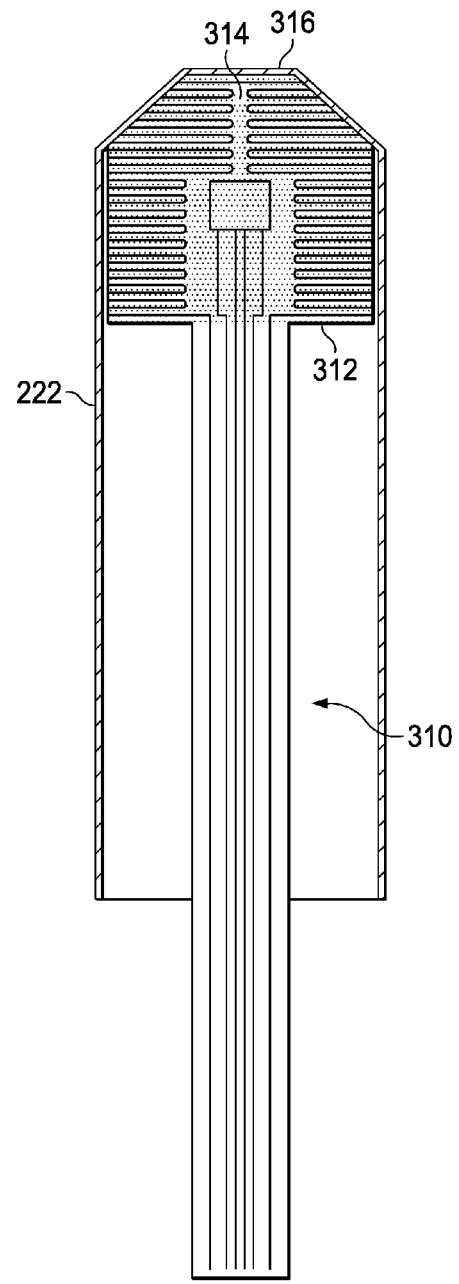

FIG. 3C illustrates another example embodiment of a flexible circuit 310 in accordance with aspects of the present invention.

As shown in the figure, flexible circuit 310 is different from flexible circuit 220, such that it can better conform to the shape of probe tip 222. In particular, head portion 312 includes tapered end 314 to match tapered end 316 of probe tip 222.

Previous methods of disposing a heating element and temperature sensor into the probe tip required operators to painstakingly adhere the elements to the inner surface of the probe tip. This required the use of small tools to enable the operator to position the parts properly within the probe tip. The conventional method was manually limited and precise replication from one assembled device to another was non-existent. It can be compared to making a ship in a bottle, each one is painstaking slow in assembly and each resulting assembly is slightly different from the next.

In accordance with aspects of the present invention, the heating element and temperature sensor, being attached to the flexible base, are inserted into the probe tip using an inflatable member. This method may be automated, thus increasing assembly speed and increasing precision and duplication. In one example method, the head portion of the flexible circuit may be wrapped around the inflatable member, which is inserted into the probe tip and then inflated. Inflating the inflatable member serves to push the head portion of the flexible base against the inner wall of the probe tip, such that the head portion conformingly adheres to the curved inner surface of the probe tip. This will now be further described with reference to FIGS. 4A-B.

FIG. 4A illustrates an insertion component in a first configuration, used in manufacturing a temperature sensing device in accordance with aspects of the present invention.

As shown in the figure, insertion component 400 includes outer tube 402, inner tube 404, seal flange 406 and inflatable portion 408.

Outer tube 402 and inner tube 404 may be constructed from metal, plastic, or any other material that can resist expansion under pressure or vacuum that is sufficient to inflate inflatable portion 408. Outer tube 402 is operable to connect to seal flange 406 and provide a conduit through which vacuum can be pulled. Inner tube 404 is operable to connect to inflatable portion 408 and provide a conduit through which fluid may be used to inflate inflatable portion 408.

Seal flange 406 is connected to outer tube 402 and is operable to create a seal when it is pressed against a mating surface. Seal flange 406 may be made of rubber, silicone, or any other material suitable to create a seal.

Inflatable portion 408 is connected to inner tube 404 and is operable to inflate when positive pressure is provided inside inflatable portion 408, when negative pressure is provided outside inflatable portion 408, or a combination of both. Inflatable portion 408 may be made of a compliant or non-compliant material. If a compliant material is used, the walls of inflatable portion 408 will stretch as it is inflated, thus it may be beneficial to use a compliant material if probe tips of different diameters are being produced. Thus, a single insertion component could be used to manufacture multiple sizes of probe tips. A non-limiting example of a compliant material is latex. If a non-compliant material, such as nylon, is used, the walls of inflatable portion 408 will not stretch as it is inflated. Instead, inflatable portion 408 would be created such that, when fully inflated, the outer diameter of inflatable portion 408 is substantially equivalent to the inner diameter of the probe tip. In a manufacturing process, this may be beneficial because the inflatable portion, when inflated with a specific volume of inflation material, will reach the same inflated size every time. This leads to a repeatable, reliable assembly process when one size probe tip is being manufactured. A non-limiting example of a non-compliant material is nylon.

The operation of insertion component 400 is further described with reference to FIG. 4B.

FIG. 4B illustrates insertion component 400 in a second configuration, used in manufacturing a temperature sensing device in accordance with aspects of the present invention.

As shown in the figure, inflatable portion 408 is in an expanded configuration. The expansion can occur based on a pressure differential between the volume within inner tube 404 and the volume between inner tube 404 and outer tube 402.

In one embodiment, inflatable portion 408 expands as pressure is introduced through inner tube 404. For example, the pressure within inner tube 404 increases when fluid is introduced into inner tube 404, as shown by the arrow marked "A". As pressure within inner tube 404 increases, the diameter of inner tube 404 does not increase. In contrast, the same pressure in inner tube 404 will be present in the interior volume of inflatable portion 408, as inner tube 404 and inflatable portion 408 are in fluid communication with each other. As pressure increases in the interior volume of inflatable portion 408, inflatable portion 408 will expand. Any fluid may be used non-limiting examples of which include air and water.

In another embodiment, inflatable portion 408 expands when pressure decreases in the volume between inner tube 404 and outer tube 402. For example, the pressure in the volume between inner tube 404 and outer tube 402 may decrease by suctioning air through outer tube 402 (as shown by the arrow marked "B"), while seal flange 406 is properly sealed against another surface. Expanding inflatable portion 408 in this manner may require inner tube 404, outer tube 402 and the surface against which seal flange 406 is sealed to be rigid in order to maintain structural rigidity under suction.

In another embodiment, a combination of pressurized fluid and suction may be used together in order to inflate the inflatable member to the desired size. For example, the pressure in the volume within inner tube 404 may be increased by introducing fluid into inner tube 404, as shown by the arrow marked "A," and the pressure in the volume between inner tube 404 and outer tube 402 may be decreased by suctioning air through outer tube 402 (as shown by the arrow marked "B"), while seal flange 406 is properly sealed against another surface.

Insertion component 400 is used to conformingly affix flexible circuit 218 to the curved inner surface of probe tip 222 as will be described in more detail with reference to FIGS. 5A-F.

Figure 5A:
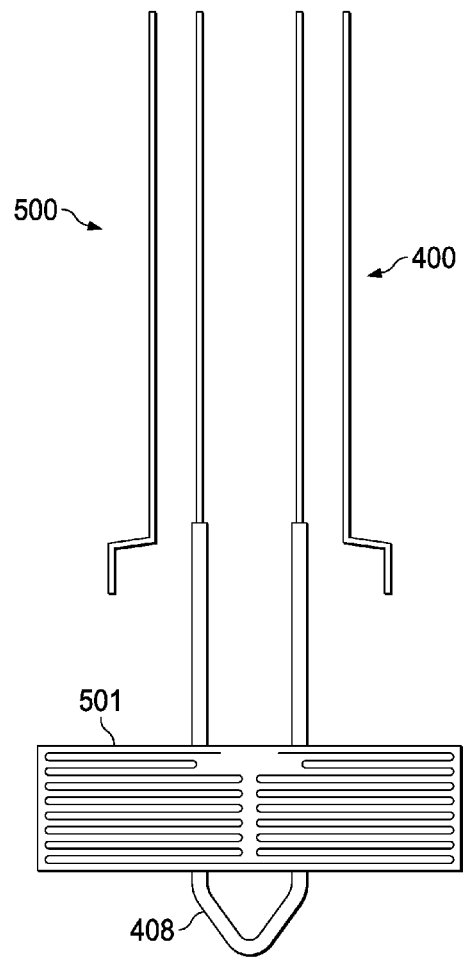
FIGS. 5A-F illustrate an assembly process employed to assemble a temperature sensing device in accordance with aspects of the present invention.

FIG. 5A illustrates a first step of assembling a temperature sensing device in accordance with aspects of the present invention. (Shows the heater element.)

As shown in the figure, system 500 includes flexible circuit 591 and insertion component 499. Flexible circuit 591 is disposed against inflatable portion 498 in preparation for deployment of flexible circuit 591. In some embodiments, the surface of flexible circuit 501 may be coated with an adhesive in order to maintain contact between flexible circuit 501 and inflatable portion 408. The adhesive layer will be described in greater detail with reference to FIG. 5B. The adhesive used for this purpose should be relatively weak as compared to adhesive layer 214, which is coated on the surface of flexible circuit 220 that is not in contact with inflatable portion 408.

Figure 5C:
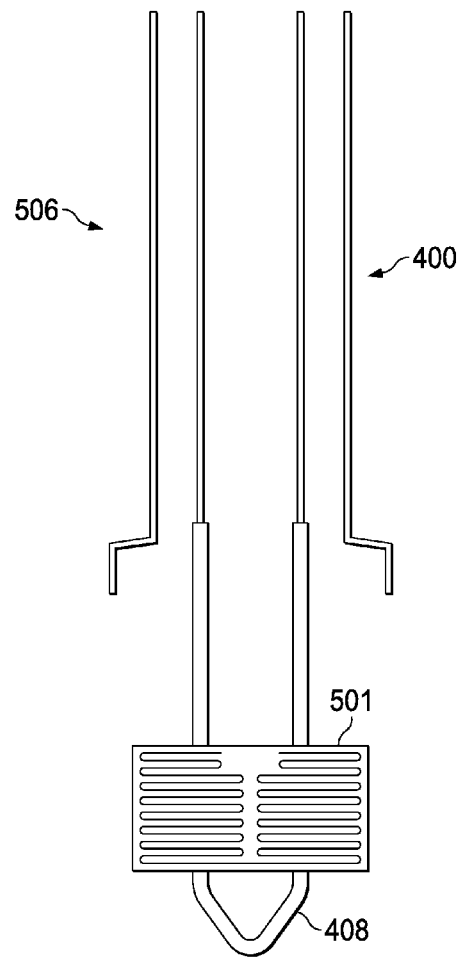
Figure 5B:
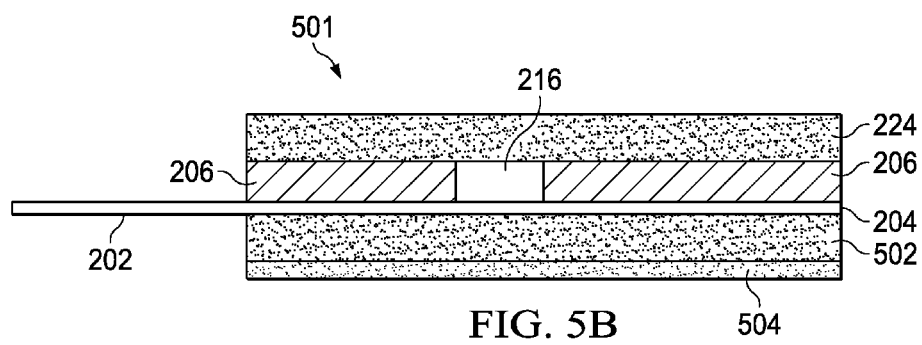

FIG. 5B illustrates a cross sectional view of flexible circuit 501.

As shown in the figure, flexible circuit 501 includes all of the elements discussed with reference to flexible circuit 218, but also includes adhesive 502 and peel-off layer 504.

Adhesive 502 is a stronger adhesive than adhesive 224, and enables flexible circuit 501 to stick to another surface. Once adhesive layer 502 deposited on head portion 204, in some embodiments, peel-off layer 504 may be added. In this manner, flexible circuit 501 can be mass manufactured with peel-off adhesives. When flexible circuit 501 is to be added or inserted into a probe tip, the peel-off layer can be removed so adhesive layer 502 can be conformingly attached to the curved inner surface of the probe housing. Employing this method will allow for a plurality of flexible circuit boards to be prefabricated and stored, such that the peel-off layer can be removed at the time of assembly. The attachment process will be further described with reference to FIGS. 5C-E.

Figures 5D, 5E:
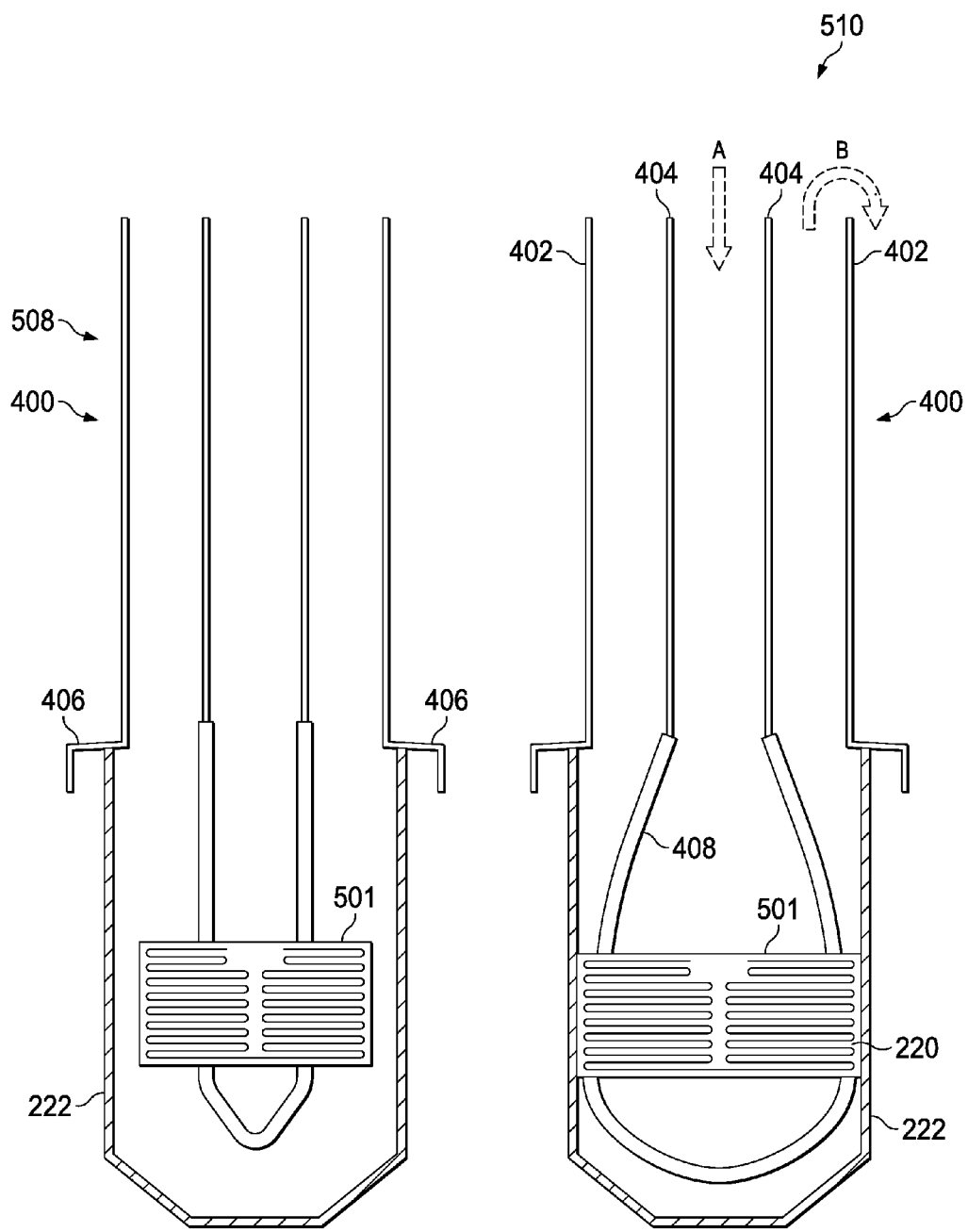

In other embodiments, once adhesive 504 is applied to head portion 204, flexible circuit 501 can be inserted and attached to the inside of the probe housing. In this embodiment the entire device is made at one time (there is no need to store a plurality of ready to use flexible circuits as discussed above). With reference to FIGS. 5C-E, it is assumed that the peel-off layer has ahead been removed.

FIG. 5C illustrates the second step of assembling a temperature sensing device in accordance with aspects of the present invention.

As shown in the figure, system 506 includes flexible circuit 501 and insertion component 400. In this step, flexible circuit 501 is wrapped around inflatable portion 408. Weak adhesive layer 224 will serve to adhere flexible circuit 501 to inflatable portion 408.

FIG. 5D illustrates the third step of assembling a temperature sensing device in accordance with aspects of the present invention.

As shown in the figure, system 508 includes flexible circuit 501, insertion component 400 and probe tip 222. In this step, the assembly of the wrapped flexible circuit 501 and insertion component 400 is inserted into probe tip 222. Insertion is continued until seal flange 406 contacts and seals against probe tip 222.

FIG. 5E illustrates the fourth step of assembling a temperature sensing device in accordance with aspects of the present invention.

As shown in the figure, system 510 includes insertion component 400 in an expanded state, flexible circuit 501 and probe tip 222. In an example embodiment, an operator will inflate inflatable portion 408 by either introducing fluid through inner tube 404 (shown by arrow "A"), suctioning fluid through outer tube 402 (shown by arrow "B"), or using some combination thereof. Inflatable portion 408 will continue to be expanded until flexible circuit 501 contacts the inner surface of probe tip 222, thus putting adhesive 502 in contact with the inner surface of probe up 222 as well. Adhesive 502 adheres to the inner surface of probe tip 222.

Figure 5F:
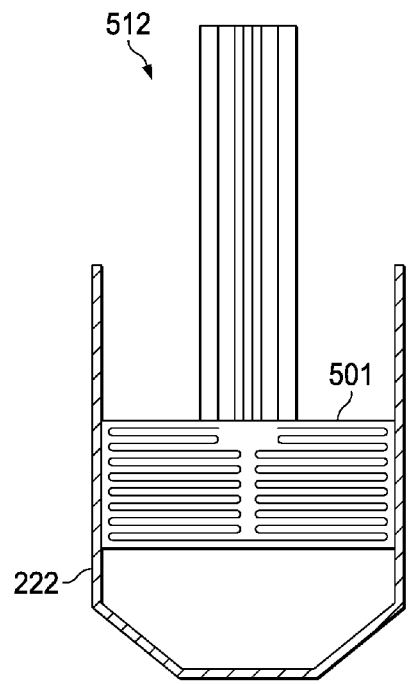

FIG. 5F illustrates the fifth step of assembling a temperature sensing device in accordance with aspects of the present invention.

As shown in the figure, system 512 includes flexible circuit 501 and probe tip 222. In this step, inflatable member 408 has been deflated and removed from probe tip 222, leaving flexible circuit 501 adhered to the inner surface of probe tip 222. The process of deflating inflatable member 408 includes detaching inflatable member 408 from flexible circuit 220. As discussed with reference to FIG. 5A, adhesive layer 224 between inflatable member 408 and flexible circuit 501 provides a weak bond as compared to adhesive layer 502 between flexible circuit 501 and the inner surface of probe tip 222. Thus, when inflatable member 408 is deflated, the weak bond between inflatable member 408 and flexible circuit 501 is broken, allowing insertion component 400 to be removed, leaving flexible circuit 501 attached to the inner surface of probe tip 222.

Figure 5G:
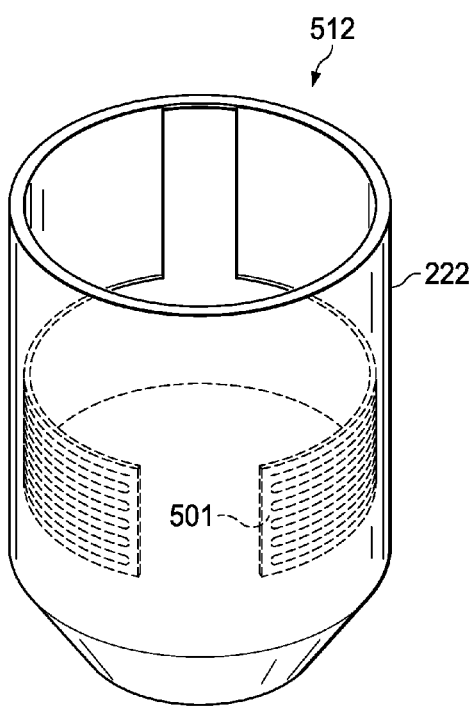
FIG. 5G illustrates an alternate view of FIG. 5F.

FIG. 5G illustrates an alternate view of the system in FIG. 5F.

As shown in the figure, a 3-dimensional view of system 512 is shown. It can be appreciated that, while inflatable member 408 is expanding as shown in FIG. 5E, flexible circuit 501 is deforming so as to conform to the curved inner surface of probe tip 222. As a non-limiting example, the two free ends of flexible circuit 501 may be in contact with one another when flexible circuit 501 is wrapped around inflatable member 408 in the deflated configuration. As inflatable member 408 is expanded, however, the two free ends of flexible circuit 501 will move apart from each other, and will continue to move apart until flexible circuit 501 contacts the inner surface of probe tip 222. As shown in FIG. 5G, flexible circuit 501 does not contact the inner surface of probe tip 222 over its hill circumference due to the expansion discussed above. The amount of contact, though, is still sufficient for preheating probe tip 222 as needed.

Conventional assembly methods typically employ a single rigid heating element to preheat the probe tip. In many cases rigid heating element has a flat surface for affixing to the curved inner surface of the probe tip. Accordingly, to reduce the space between the flat surface of the rigid heating element and the curved inner surface of the probe tip, the affixing surface of the rigid heating element is minimized. This minimized surface area inefficiently preheats the probe tip, because the heat must radiate from the relatively small single rigid heating element surface area. Furthermore, the conventional assembly methods are typically manual, which results in imprecise duplication of heating element placement.

In contrast, flexible circuit 220 of the present invention conformingly attaches to the inner surface of probe tip 216, thus disposing heating element 202 over a large portion of the inner surface of probe tip 216. The coil arrangement of heating element 202 allows for it to be in contact with much more surface area of the inner surface of probe tip 216 than the heating element of the prior art, and therefore it provides for more efficient preheating of probe tip 216. In addition, because heating element 202 and temperature sensor 212 are disposed on flexible circuit 220 prior to insertion into probe tip 216, the assembly method is much simpler. Furthermore, an assembly method in accordance with aspects of the present invention may be automated, which results in very imprecise duplication of heating element placement.

Figure 5H:
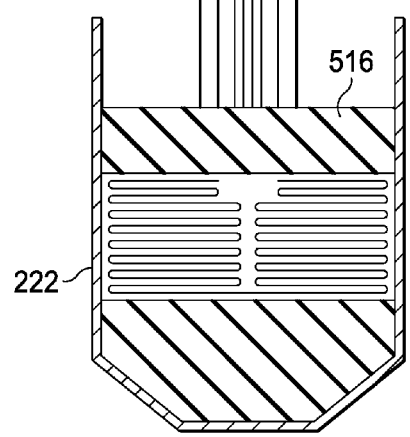
FIG. 5H illustrates an alternate embodiment of the assembly process referenced in FIGS. 5A-E.

FIG. 5H illustrates another embodiment of the system in FIG. 5F.

As shown in FIG. 5G, system 514 includes probe tip 222, flexible circuit 501 and heat insulating material 516.

Heat insulating material 516 may include curable insulating materials, expandable insulating materials, or any other insulating materials that could be applied inside probe tip 222, provided that the materials used do not erode or degrade the circuit assembly.

Insulating material 516 serves multiple purposes. First, it may provide support to flexible circuit 501 to maintain contact between flexible circuit 501 and the inner diameter of probe tip 222. Thus, if adhesive layer 502 failed at some point and no longer was able to keep flexible circuit 501 in contact with the inner surface of probe tip 222, heat insulating material 516 would prevent flexible circuit 501 from losing contact with the inner surface of probe tip 222. Second, heat insulating material 516 may help maintain probe tip 222 at a preheated temperature for a longer period of time, thus reducing the amount of power required to maintain the preheated temperature.

FIG. 5I illustrates a final assembly of a temperature sensing device in accordance with aspects of the present invention.

As shown in the figure, system 518 includes flexible circuit 501, probe tip 222, and probe 104. System 518 is also shown as including optional heat insulating material 516.

Probe 104 may be attached to probe tip 222 using standard joining methods, non-limiting examples of winch include adhesives, welding, soldering, mechanical fasteners, or any other joining method that would serve to connect probe 104 to probe tip 222 in a reliable and repeatable fashion. Probe 104 can then be attached to probe housing 102 (not shown) using standard attachment methods or mechanisms.

As described above, temperature sensor 212 is located in probe tip 222, however in other embodiments the temperature sensor is not required to be at the probe tip, thus further simplifying the assembly process. In some embodiments, the temperature sensor is an infrared thermal detector that may be located elsewhere in the assembly. The infrared thermal detector will be designed to detect the temperature of probe tip 222 by sensing the infrared radiation emitted from the inner surface of probe tip 222. An example embodiment wherein the temperature sensor is not disposed at the probe tip will now be described in greater detail with reference to FIG. 6.

FIG. 6 illustrates an alternate assembly configuration for a temperature sensing device in accordance with aspects of the present invention.

As shown in the figure, system 600 includes probe housing 602, infrared sensor 604, probe 104, probe tip 222, heating element 206 and flexible circuit 606.

Probe housing 602 is very similar to probe housing 102 (not shown), however it includes a space in which to mount infrared sensor 604.

Infrared sensor 604 may be any standard infrared sensor that utilizes pyroelectric or ferroelectric materials, or that utilizes micro bolometer technology.

Flexible circuit 606 is substantially similar to flexible circuit 501, however it does not include a temperature sensor, it only includes heating element 206, as the temperature sensor from flexible circuit 501 was replaced by infrared sensor 604.

In operation, when probe tip 222 is placed at the site where the temperature reading is desired, infrared sensor 604 would sense the temperature at probe tip 222 and relay the temperature to the display module (not shown). This configuration would further simplify the assembly process by eliminating the need to provide a temperature sensor as part of flexible circuit 606.

In prior art temperature sensing devices, the assembly method is tedious, time-consuming, and not particularly reliable or repeatable. The assembly method is dependent on skilled operators manually attaching a heating element and temperature sensor to the inner surface of a probe, which is akin to assembling a ship in a bottle. In addition, the heating element does not necessarily conform to the inner surface of the probe, reducing the heating efficiency by reducing the amount of surface area in which the heating element is in contact with the inner surface of the probe tip.

The present invention provides several methods of assembling a temperature sensing device that overcomes the limitations of the prior art. The heating element and temperature sensor are disposed on the head portion of a flexible circuit base. This allows for the heating element to cover the majority of the head portion of the flexible circuit base, while the temperature sensor covers the remaining space of the head portion. The head portion of the flexible circuit base is then wrapped around an inflatable member and inserted into the probe tip. The inflatable member is then inflated, expanding the head portion of the flexible circuit base until the head portion conformingly attaches to the curved inner surface of the probe tip. The inflatable member is then deflated and removed, thus leaving the assembled probe tip ready for further operations to attach the tip to the rest of the temperature sensing device using standard methods.

The assembly method in accordance with aspects of the present invention provides for more efficient, uniform preheating of the probe tip because the heating element is conformingly attached to the curved inner surface of the probe tip, thus providing a larger surface area for preheating. In addition, the method of using an inflatable member to attach the flexible circuit to the probe tip eliminates the need for highly skilled workers, and provides a much more reliable and repeatable process with which a temperature sensing device may be manufactured.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A device comprising:
   a housing having an inner surface with a first end and a second end;
   a flexible heating component surrounded by the inner surface and near the first end; and
   a power line coupled to the flexible heating component and extending to the second end; and
   a temperature sensor including an infrared detector disposed within the housing near the first end; and
   a thermal insulating material disposed within the housing near the first end, the thermal insulating material maintaining the flexible heating component with the inner surface.

2. The device of claim 1, wherein the flexible heating component surrounds the temperature sensor.

3. The device of claim 1, wherein the flexible heating component is coplanar with the temperature sensor.

* * * * *